(12) United States Patent
Al Attar

(10) Patent No.: US 9,511,105 B1
(45) Date of Patent: Dec. 6, 2016

(54) PILES TREATMENT

(71) Applicant: Mohamed Jihath Mohammad Jamal Al Attar, Al Madinah Al Munawarah (SA)

(72) Inventor: Mohamed Jihath Mohammad Jamal Al Attar, Al Madinah Al Munawarah (SA)

( * ) Notice: Subject to any disclaimer, the term of this patent is extended or adjusted under 35 U.S.C. 154(b) by 0 days.

(21) Appl. No.: 15/219,231

(22) Filed: Jul. 25, 2016

(51) Int. Cl.
| | |
|---|---|
| *A01N 65/00* | (2009.01) |
| *A61K 36/534* | (2006.01) |
| *A61K 9/00* | (2006.01) |
| *A61K 9/06* | (2006.01) |
| *A61K 36/88* | (2006.01) |
| *A61K 36/71* | (2006.01) |
| *A61K 35/35* | (2015.01) |
| *A61K 36/889* | (2006.01) |
| *A61K 9/02* | (2006.01) |
| *A23F 3/14* | (2006.01) |

(52) U.S. Cl.
CPC ............... *A61K 36/534* (2013.01); *A23F 3/14* (2013.01); *A61K 9/0053* (2013.01); *A61K 9/0095* (2013.01); *A61K 9/02* (2013.01); *A61K 9/06* (2013.01); *A61K 35/35* (2013.01); *A61K 36/71* (2013.01); *A61K 36/88* (2013.01); *A61K 36/889* (2013.01)

(58) Field of Classification Search
CPC ....................................................... A61K 36/00
USPC ........................................................ 424/725
See application file for complete search history.

(56) References Cited

U.S. PATENT DOCUMENTS

2011/0319364 A1* 12/2011 Wegner .................. A01N 25/16
514/102

* cited by examiner

*Primary Examiner* — Michael Meller
(74) *Attorney, Agent, or Firm* — Charles L. Thoeming

(57) ABSTRACT

The present invention provides ointment, suppository, and herbal tea modalities for the treatment of hemorrhoids. The ointment and suppository modalities include the extracts of *Nigella sativa*, leek seed powder, Adeps camel, cow butter oil (Friesian), cow butter oil (Jersey), water buffalo butter oil, sheep butter oil, goat butter oil, coconut oil, and farm cow butter oil. The herbal tea modalities include *Mentha piperita*, Peppermint (American *Mentha*), *Mentha aquatic*, and *Mentha longifolia* (Moroccan mint).

12 Claims, No Drawings

PILES TREATMENT

CROSS-REFERENCES TO RELATED APPLICATIONS

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BT-REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable.

STATEMENT REGARDING COPYRIGHTS/TRADEMARKS

Portions of the disclosure of this patent document contain material which is subject to copyright/trademark protection. The copyright/trademark owner has no objection to the facsimile reproduction by anyone of the patent document or the patent disclosure, as it appears in the United States Patent and Trademark Office patent file or records, but otherwise reserves all copyright and trademark rights whatsoever.

BACKGROUND OF THE INVENTION

Field of the Invention

The invention pertains to remedies for piles, commonly known as hemorrhoids. More specifically, ointment, suppository and tea modalities that are prepared using a variety of natural materials, such as herbal plants and natural extracts of oils, butters and animal fats, which have beneficial effects including relief from hemorrhoid pain and suffering, improvement of health by eradicating the hemorrhoid disease by continuous use, successful treatment for hemorrhoids by using natural plants and products without preserving materials or chemicals, successful treatment of the hemorrhoids without surgery, providing gentle hemorrhoid remedies without any unwarranted side effects, and suitable treatment for pregnant women without the risks associated with existing pharmaceutical therapies.

Description of Related Art Including Information Disclosed Under 37 CFR 1.97 and 1.98

Conventional compositions have been largely restricted to alleviating the symptoms associated with hemorrhoids but have been found unsatisfactory as regards the healing thereof. For example, international application WO 2004/073757 A1 discloses an anal treatment pad to which a skin care composition comprising zinc oxide, niacinamide and hexamidine are applied. However, even the repeated application of such a composition will not result in a substantial regression of hemorrhoids.

BACKGROUND OF THE INVENTION

Constipation is infrequent bowel movements (typically three times or fewer per week), difficulty during defecation (straining during more than 25% of the bowel movements or a subjective sensation of hard stools), or the sensation of incomplete bowel evacuation.

Constipation is a symptom with many causes. These causes are of two types: obstructed defecation and colonic slow transit (or hypomobility). Causes of colonic slow transit constipation include diet, hormones, side effects of medications, and heavy metal toxicity. One of the main problems of constipation is the pain. Straining during bowel movements due to constipation may cause many issues. Hemorrhoids often may develop due to colonic slow transit constipation, as can anal fissures, and rectal bleeding. Rectal prolapse, though rare, may occur, a condition where a piece of intestinal lining pushes from the anal opening. Constipation may also result in stool packing the intestine so tightly that it cannot be expelled, resulting in a condition called fecal impaction.

The colon is a breeding ground for both good and bad bacteria. When too much fermentation and putrefaction is produced in the colon by neglecting to keep it in good condition, it is necessary for the waste to be expelled from the body. And that is exactly why the healthy colon is well-equipped with a very efficient system of elimination. But the colon only functions adequately and efficiently if it is in good working order. In a healthy colon environment, the good bacteria will control the bad. But in an unhealthy environment, the bad bacteria rule.

Constipation often is symptomatic of an unhealthy colon because toxins are formed and absorbed when waste remains in the intestines. If we don't eliminate toxins through our bowels properly, they will just sit in the body, allowing toxins to seep back into the blood stream, increasing the toxic load of the body.

Symptoms of constipation include pain, swollen abdomen or abdominal pain, and infrequent or difficulty in eliminating. Constipation can aggravate such issues as high cholesterol, obesity, diabetes, and weight gain.

Hemorrhoids are painful, round swelling formed under the lining of the mucous membrane of the outer part of the rectum due to expansion of blood vessels, particularly veins.

It would be desirable to prepare an organic, natural formulation protocol for ointments, suppositories, and teas which would singularly, or in combination, act to promote healthy function of the intestines, clean the body of toxins, allow a free flow of energy, tone and nourish intestines and colon, slow the aging process for the intestines and colon, and calm and relax the body in general, and the digestive system in particular.

It would be further desirable that the organic, natural formulation protocol for ointments, suppositories, and teas for the treatment of hemorrhoids not include any preservatives or pharmaceuticals, and that regular use of these organic, natural ointments, suppositories, and teas would obviate the necessity for surgery to treat the hemorrhoids.

It is an object of the invention to provide a composition, a method for manufacture of a composition, and uses of a composition which may overcome the limitations of the prior art with respect to the healing of hemorrhoids.

The inventor has found that the deficiencies of the conventional composition may, according to a first aspect, be overcome by a tea supplement comprising aqueous extracts of at least those selected from the group consisting of *mentha piperita*, peppermint (American *mentha*), *mentha aquatic*, and *mentha longifolia* (Moroccan mint). These extracts are active agents and combine synergistically. All four ingredients may, but need not be present.

According to another aspect, the invention provides a method for the manufacture of an ointment useful in the treatment of hemorrhoids including extracts of *Nigella sativa*, leek seed powder, Adeps camel, cow butter oil (Friesian), cow butter oil (Jersey), water buffalo butter oil, sheep butter oil, goat butter oil, coconut oil, and farm cow butter oil.

Also, according to further aspects, the invention provides the use of a suppository including extracts of *Nigella sativa*, leek seed powder, Adeps camel, cow butter oil (Friesian), cow butter oil (Jersey), water buffalo butter oil, sheep butter oil, goat butter oil, coconut oil, and farm cow butter oil.

It has been found that upon several applications of the inventive ointment and/or suppositories together with the tea medicament, respectively, hemorrhoids will significantly regress and eventually vanish. The effectiveness of the applicant's invention

BRIEF SUMMARY OF THE INVENTION

Accordant with the present invention, there has been discovered an organic and natural herbal cleanse formulation protocol which is useful for eliminating parasites, promoting healthy function of the intestines, cleaning the body of toxins, creating a free flow of energy, toning and nourishing the body, slowing the aging process, and calming and relaxing the body. The herbal cleanse formulation comprises herbal formulations which are to be taken in various modalities at specific times of the day for a determined number of consecutive days in a specific protocol.

The organic, natural formulations include suppository, ointment, and tea modalities which can be used separately or together to treat hemorrhoids depending upon the severity of the affliction.

The formulations for suppository modalities include extract of *Nigella sativa*, extract of leek seed powder, extract of Adeps camel, extract of cow butter oil (Friesian), extract of cow butter oil (Jersey), extract of water buffalo butter oil, extract of sheep butter oil, extract of goat butter oil, extract of coconut oil, and extract of farm cow butter oil.

The formulations for ointment modalities include extract of *Nigella sativa*, extract of leek seed powder, extract of Adeps camel, extract of cow butter oil (Friesian), extract of cow butter oil (jersey), extract of water buffalo butter oil, extract of sheep butter oil, extract of goat butter oil, extract of coconut oil, and extract of farm cow butter oil.

The formulations for tea modalities include *mentha piperita*, peppermint (American *mentha*), *mentha aquatic*, and *mentha longifolia* (Moroccan mint).

The herbal cleanse formulation protocol of the tea modalities of the present invention is particularly useful for cleaning toxins and congestion, eliminating parasites, promoting healthy function of the intestine, creating a free flow of energy, toning and nourishing the intestines and colon, slowing the digestive system aging process, and calming and relaxing the digestive system. As such, it may be used alone, or in conjunction with the ointment and/or suppository modalities to relieve the symptoms of hemorrhoids, and reduce or eliminate the presence of hemorrhoids.

BRIEF DESCRIPTION OF THE SEVERAL VIEWS OF THE DRAWINGS

There are no drawings.

DETAILED DESCRIPTION OF THE INVENTION

DEFINITIONS—The following definitions are provided for terms used in this disclosure:

Ghee is a class of clarified butter. Grass-fed organic Ghee is made from the milk of pastured cows, sheep, goats, or water buffalo, fed on fresh green grass in spring and fall only. The one and only ingredient is milk, with absolutely nothing else added to it.

Extract of *Nigella sativa* (black-caraway, also known as *nigella* or kalonji), often called black cumin, is an annual flowering plant in the family Ranunculaceae, native to south and southwest Asia. *Nigella sativa* grows to 20-30 cm (7.9-11.8 inches) tall, with finely divided, linear (but not thread-like) leaves. The flowers are delicate, and usually colored pale blue and white, with five to ten petals. The black caraway fruit is a large and inflated capsule composed of three to seven united follicles, each containing numerous seeds which are used as spice, sometimes as a replacement for black cumin (*Bunium bulbocastanum*).

Extract of Adeps camel is the fat of the female camel.

Extract of cow butter oil (Friesian) (also known as Ghee). "Friesian" denotes animals of a traditional European ancestry, bred for both dairy and beef use.

Extract of cow butter oil (Jersey) (also known as Ghee). "Jersey" cattle are a small breed of dairy cattle. Originally bred in the Channel Island of Jersey, the breed is popular for the high butterfat content of its milk and the lower maintenance costs attending its lower bodyweight, as well as its genial disposition.

Extract of water buffalo butter oil (also known as Ghee). Water buffalo or domestic Asian water buffalo (*Bubalus bubalis*) is a large bovid originating in South Asia, Southeast Asia, and China. Today, it is also found in Europe, Australia, and some American countries. The wild water buffalo (*Bubalus arnee*) native to Southeast Asia is considered a different species, but most likely represents the ancestor of the domestic water buffalo.

*Mentha piperita* (also known as *M. balsamea* Wild) as used in this disclosure shall mean a hybrid mint, a cross between watermint and spearmint. The plant, indigenous to Europe and the Middle East, is now widespread in cultivation in many regions of the world. It is found wild occasionally with its parent species.

Peppermint (American *mentha*) (syn. *M. arvensis* var. *canadensis*) as used in this disclosure shall mean a species of mint commonly known as American wild mint, native to North America (from Northwest Territories to central Mexico), eastern Asia (Siberia to Java) and the Northern Territory of Australia. The flowers are bluish or a slight violet tint. The plant is upright about 4 inches (10 cm) to 18 inches (46 cm) tall. Leaves grow opposite from each other, and flower bunches appear at the upper leaf axil. The mint grows in wet areas but not directly in water, so it will be found near sloughs, lake and river edges. Flowers bloom from July to August. The related species *Mentha canadensis* is also included in *Mentha arvensis* by some authors as two varieties, *M. arvensis* var. *glabrata* Fernald (in reference to North American plants) and *M. arvensis* var. *piperascens* Malinv. ex L. H. Bailey (in reference to eastern Asian plants).

*Mentha aquatic* (water mint; syn. *Mentha hirsuta* Huds.) as used in this disclosure shall mean a perennial plant in the genus *Mentha*, that grows in damp places and is native to much of Europe, northwest Africa and southwest Asia.

*Mentha longifolia* (Moroccan mint) (Horse Mint; syn. *M. spicata* var. *longifolia* L., *M. sylvestris* L., *M. tomentosa* D'Urv, *M. incana* Willd.) as used in this disclosure shall mean a species in the genus *Mentha* (mint) native to Europe, western and central Asia (east to Nepal and the far west of China), and northern and southern (but not tropical) Africa. It is a very variable herbaceous perennial plant with a peppermint-scented aroma. Like many mints, it has a creeping rhizome, with erect to creeping stems 40-120 cm tall. The leaves are oblong-elliptical to lanceolate, 5-10 cm long and 1.5-3 cm broad, thinly to densely tomentose, green to greyish-green above and white below. The flowers are 3-5 mm long, lilac, purplish, or white, produced in dense clusters (verticillasters) on tall, branched, tapering spikes; flowering in mid to late summer. It spreads via rhizomes to form clonal colonies.

The actual treatment of hemorrhoids, for which the present invention is helpful, includes a twice-daily application of the ointment and suppositories to the anus (inside and peripherally). It is preferable to apply the ointment once in the morning, after defecation, and once again directly before going to sleep. In a preferred embodiment, a package contains about 20 suppositories, each containing 2 to 3 ml, preferably 2.5 ml of the ointment, sufficient for about 10 days of treatment. Assuming that one package of the ointment contains about 50 cm., according to the degree (I-IV) of the hemorrhoids, one to four packages will have to be consumed. The degree (I-IV) of hemorrhoids may be defined in the following.

There are two kinds of hemorrhoids, namely inside (internal) hemorrhoids, the symptoms of which are bleeding, pain, and distensibility; and outside (external) hemorrhoids, the symptoms of which, in the first stage (degree 1), are burning and itching. In a second stage (degree II), the hemorrhoids may come out during defecation, and slip back by themselves thereafter. In a third stage (degree III), the hemorrhoids have to be pushed back inside after defecation. In a fourth, most severe stage (degree IV), the hemorrhoids remain outside, and it is no longer possible to push them back inside.

In order to assist the treatment, it is desirable that the patient should not suffer from constipation. It is preferable that, accompanying the treatment, the patient mainly consumes fibrous nourishments such as fruit and vegetables. It is further helpful if the patient consumes dry foods, particularly leguminous plants, and at least 1.5 l of water daily. Particularly preferable is a diet containing fresh or dried apricots, fresh or dried plums, flax seed, yogurt, and/or cherries. Preferable beverages include the therapeutic tea of the present invention.

An embodiment of the intestinal tea kit for treating hemorrhoids includes *mentha piperita*, peppermint (American *mentha*), *mentha aquatic*, and *mentha longifolia* (Moroccan mint).

An embodiment of the intestinal tea kit for treating hemorrhoids includes 33 grams of *mentha piperita*, 20 grams of peppermint (American *mentha*), 25 grams of *mentha aquatic*, and 22 grams of *mentha longifolia* (Moroccan mint).

An embodiment of the intestinal tea kit for treating hemorrhoids includes 33 weight percent *mentha piperita*, 20 weight percent peppermint (American *mentha*), 25 weight percent *mentha aquatic*, and 22 weight percent of *mentha longifolia* (Moroccan mint).

An embodiment of the intestinal tea kit for treating hemorrhoids is contained in a porous tea bag, and the tea bag is placed into about 8 ounces of hot water for three to five minutes to provide a hot tea to be ingested orally.

An embodiment of the intestinal tea kit for treating hemorrhoids includes a concentration of *mentha piperita* that comprises about 33 weight percent of the intestinal tea.

An embodiment of the intestinal tea kit for treating hemorrhoids includes a concentration of peppermint (American *mentha*) that comprises about 20 weight percent of the intestinal tea.

An embodiment of the intestinal tea kit for treating hemorrhoids includes a concentration of *mentha aquatic* that comprises about 25 weight percent of the intestinal tea.

An embodiment of the intestinal tea kit for treating hemorrhoids includes a concentration of *mentha longifolia* (Moroccan mint) that comprises about 22 weight percent of the intestinal tea.

An embodiment of an herbal cleanse tea formulation for treating hemorrhoids includes *Mentha piperita*, Peppermint (American *Mentha*), *Mentha aquatic*, and *Mentha longifolia* (Moroccan mint).

An embodiment of an herbal cleanse tea formulation for treating hemorrhoids includes 33 grams of *mentha piperita*, 20 grams of peppermint (American *mentha*), 25 grams of *mentha aquatic*, and 22 grams of *mentha longifolia* (Moroccan mint).

An embodiment of an herbal cleanse tea formulation for treating hemorrhoids includes 33 weight percent *mentha piperita*, 20 weight percent peppermint (American *mentha*), 25 weight percent *mentha aquatic*, and 22 weight percent of *mentha longifolia* (Moroccan mint).

An embodiment of an herbal cleanse tea formulation for treating hemorrhoids includes a tea formulation that is contained in a porous tea bag, and the tea bag is placed into about 8 ounces of hot water for three to five minutes to provide a hot tea to be ingested orally.

An embodiment of an herbal cleanse tea formulation for treating hemorrhoids includes a concentration of *mentha piperita* that comprises about 33 weight percent of the intestinal tea.

An embodiment of an herbal cleanse tea formulation for treating hemorrhoids includes a concentration of peppermint (American *mentha*) that comprises about 20 weight percent of the intestinal tea.

An embodiment of an herbal cleanse tea formulation for treating hemorrhoids includes a concentration of *mentha aquatic* that comprises about 25 weight percent of the intestinal tea.

An embodiment of an herbal cleanse tea formulation for treating hemorrhoids includes a concentration of *mentha longifolia* (Moroccan mint) that comprises about 22 weight percent of the intestinal tea.

An embodiment of an herbal cleanse tea formulation for treating hemorrhoids includes tea bag preferably made of natural fabrics such as hemp cloth or pouches that allow each of the materials to be sufficiently infused into the hot water so as to extract desired ingredients, and that allows water to easily flow in or out through the bag while preventing loss of the materials, and that inhibits modification of the ingredients.

The water used to produce the tea according to the embodiments of the present invention preferably includes clean water such as first grade pure water, or pure ground water, and similar sources of pure water.

An embodiment of a formulation for treating hemorrhoids includes an ointment, the ointment providing extract of *Nigella sativa*, extract of leek seed powder, extract of Adeps camel is the fat of the female camel, extract of cow butter oil (Friesian), extract of cow butter oil (Jersey), extract of water buffalo butter oil, extract of sheep butter oil, extract of goat butter oil, extract of coconut oil, and extract of farm cow butter oil. The actual treatment of hemorrhoids, for which this embodiment is helpful, includes a twice-daily application of the ointment to the anus (inside and peripherally). It is preferable to apply the ointment once in the morning, after defecation, and once again directly before going to sleep. In an embodiment, a package contains about 20 disposable syringes or collapsible tubes with elongated ejector ducts as applicators to facilitate application of this embodiment of a formulation for treating hemorrhoids, and the related embodiments set forth below.

An embodiment of a formulation for treating hemorrhoids includes an ointment, the ointment providing 1.25 grams of extract of *Nigella sativa*, 0.75 gram of Adeps camel, 5 grams of cow butter oil (Friesian), 5 grams of cow butter oil (Jersey), 13.5 grams of extract of water buffalo butter oil, 1 gram of extract of sheep butter oil, 2 grams of extract of goat butter oil, 35 grams of extract of coconut oil, and 36 grams of farm cow butter oil.

An embodiment of a formulation for treating hemorrhoids includes an ointment, the ointment providing 1.25 weight percent of extract of *Nigella sativa*, 0.75 weight percent of Adeps camel, S weight percent of cow butter oil (Friesian), 5 weight percent of cow butter oil (Jersey), 13.5 weight percent of extract of water buffalo butter oil, 1 weight percent of extract of sheep butter oil, 2 weight percent of extract of goat butter oil, 35 weight percent of extract of coconut oil, and 36 weight percent of farm cow butter oil.

An embodiment of a formulation for treating hemorrhoids includes an ointment, the ointment providing 1.25 weight percent of extract of *Nigella sativa*.

An embodiment of a formulation for treating hemorrhoids includes an ointment, the ointment providing 0.75 weight percent of Adeps camel.

An embodiment of a formulation for treating hemorrhoids includes an ointment, the ointment providing 5 weight percent of cow butter oil (Friesian).

An embodiment of a formulation for treating hemorrhoids includes an ointment, the ointment providing 5 weight percent of cow butter oil (Jersey).

An embodiment of a formulation for treating hemorrhoids includes an ointment, the ointment providing 13.5 weight percent of extract of water buffalo butter oil.

An embodiment of a formulation for treating hemorrhoids includes an ointment, the ointment providing 1 weight percent of extract of sheep butter oil.

An embodiment of a formulation for treating hemorrhoids includes an ointment, the ointment providing 2 weight percent of extract of goat butter oil.

An embodiment of a formulation for treating hemorrhoids includes an ointment, the ointment providing 35 weight percent of extract of coconut oil.

An embodiment of a formulation for treating hemorrhoids includes an ointment, the ointment providing 36 weight percent of farm cow butter oil.

An embodiment of a formulation for treating hemorrhoids includes a suppository, the suppository providing extract of *Nigella sativa*, extract of leek seed powder, extract of Adeps camel is the fat of the female camel, extract of cow butter oil (Friesian), extract of cow butter oil (Jersey), extract of water buffalo butter oil, extract of sheep butter oil, extract of goat butter oil, extract of coconut oil, and extract of farm cow butter oil. The suppository body for this embodiment, and the following embodiments of a formulation for treating hemorrhoids, includes gelatinous suppository capsules containing a prescribed volume of the prescribed extracts. It is understood by those having ordinary skill in the art that the actual treatment of hemorrhoids, for which this suppository embodiment is helpful, includes a twice-daily application of a suppository ointment inside the anus.

An embodiment of a formulation for treating hemorrhoids includes a suppository, the suppository providing 1.25 grams of extract of *Nigella sativa*, 0.75 gram of Adeps camel, 5 grams of cow butter oil (Friesian), 5 grams of cow butter oil (Jersey), 13.5 grams of extract of water buffalo butter oil, 1 gram of extract of sheep butter oil, 2 grams of extract of goat butter oil, 35 grams of extract of coconut oil, and 36 grams of farm cow butter oil.

An embodiment of a formulation for treating hemorrhoids includes a suppository, the suppository providing 1.25 weight percent of extract of *Nigella sativa*, 0.75 weight percent of Adeps camel, 5 weight percent of cow butter oil (Friesian), 5 weight percent of cow butter oil (Jersey), 13.5 weight percent of extract of water buffalo butter oil, 1 weight percent of extract of sheep butter oil, 2 weight percent of extract of goat butter oil, 35 weight percent of extract of coconut oil, and 36 weight percent of farm cow butter oil.

An embodiment of a formulation for treating hemorrhoids includes a suppository, the suppository providing 1.25 weight percent of extract of *Nigella sativa*.

An embodiment of a formulation for treating hemorrhoids includes a suppository, the suppository providing 0.75 weight percent of Adeps camel.

An embodiment of a formulation for treating hemorrhoids includes a suppository, the suppository providing 5 weight percent of cow butter oil (Friesian).

An embodiment of a formulation for treating hemorrhoids includes a suppository, the suppository providing 5 weight percent of cow butter oil (Jersey).

An embodiment of a formulation for treating hemorrhoids includes a suppository, the suppository providing 13.5 weight percent of extract of water buffalo butter oil.

An embodiment of a formulation for treating hemorrhoids includes a suppository, the suppository providing 1 weight percent of extract of sheep butter oil.

An embodiment of a formulation for treating hemorrhoids includes a suppository, the suppository providing 2 weight percent of extract of goat butter oil.

An embodiment of a formulation for treating hemorrhoids includes a suppository, the suppository providing 35 weight percent of extract of coconut oil.

An embodiment of a formulation for treating hemorrhoids includes a suppository, the suppository providing 36 weight percent of farm cow butter oil.

The following foods and beverages should be avoided to assist the treatment: beer, wine, any kind of tinned food, black tea and coffee, any kind of roasted or fried food, tomatoes and tomato sauce or ketchup, pickles, oranges, strawberries, grapes, melons, pepper. Physical activities like walking are recommended, while siting for prolonged times should be avoided.

I claim:

1. A suppository for the therapeutic treatment of hemorrhoids, consisting essentially of therapeutically effective amounts of an extract of *Nigella sativa*, an extract of leek seed powder, an extract of Adeps camel, an extract of cow butter oil (Friesian), an extract of cow butter oil (Jersey), an extract of water buffalo butter oil, an extract of sheep butter oil, an extract of goat butter oil, an extract of coconut oil, and an extract of farm cow butter oil.

2. The suppository according to claim 1, wherein the extracts are present at 1.25 grams of extract of *Nigella sativa*, 0.75 gram of Adeps camel, 5 grams of cow butter oil (Friesian), 5 grams of cow butter oil (Jersey), 13.5 grams of extract of water buffalo butter oil, 1 gram of extract of sheep butter oil, 2 grams of extract of goat butter oil, 35 grams of extract of coconut oil, and 36 grams of farm cow butter oil.

3. The suppository according to claim 1, wherein the extracts are present at 0.25 weight percent of extract of *Nigella sativa*, 0.75 weight percent of Adeps camel, 5 weight percent of cow butter oil (Friesian), 5 weight percent of cow butter oil (Jersey), 13.5 weight percent of extract of water buffalo butter oil, 1 weight percent of extract of sheep butter oil, 2 weight percent of extract of goat butter oil, 35 weight percent of extract of coconut oil, and 36 weight percent of farm cow butter oil.

4. The suppository according to claim 1, wherein the extracts are present at 1.25 weight percent of extract of *Nigella sativa*.

5. The suppository according to claim 1, wherein the extracts are present at 0.75 weight percent of Adeps camel.

6. The suppository according to claim 1, wherein the extracts are present at 5 weight percent of cow butter oil (Friesian).

7. The suppository according to claim 1, wherein the extracts are present at 5 weight percent of cow butter oil (Jersey).

8. The suppository according to claim 1, wherein the extracts are present at 13.5 weight percent of extract of water buffalo butter oil.

9. The suppository according to claim 1, wherein the extracts are present at 1 weight percent of extract of sheep butter oil.

10. The suppository according to claim 1, wherein the extracts are present at 2 weight percent of extract of goat butter oil.

11. The suppository according to claim 1, wherein the extracts are present at 35 weight percent of extract of coconut oil.

12. The suppository according to claim 1, wherein the extracts are present at 36 weight percent of farm cow butter oil.

\* \* \* \* \*